United States Patent
Brown et al.

(10) Patent No.: US 9,486,485 B2
(45) Date of Patent: Nov. 8, 2016

(54) METHODS FOR TREATING URUSHIOL-INDUCED CONTACT DERMATITIS

(71) Applicant: Stemnion, Inc., Pittsburgh, PA (US)

(72) Inventors: Larry R Brown, Newton, MA (US); Linda O Palladino, Stormville, NY (US)

(73) Assignee: STEMNION, INC., Pittsburgh, PA (US)

( * ) Notice: Subject to any disclaimer, the term of this patent is extended or adjusted under 35 U.S.C. 154(b) by 43 days.

(21) Appl. No.: 14/201,980

(22) Filed: Mar. 10, 2014

(65) Prior Publication Data

US 2014/0271910 A1    Sep. 18, 2014

Related U.S. Application Data

(60) Provisional application No. 61/792,031, filed on Mar. 15, 2013.

(51) Int. Cl.
| | | |
|---|---|---|
| *A61K 38/18* | (2006.01) | |
| *A61K 35/50* | (2015.01) | |
| *A61K 38/19* | (2006.01) | |
| *A61K 35/54* | (2015.01) | |

(52) U.S. Cl.
CPC .................................. *A61K 35/50* (2013.01)

(58) Field of Classification Search
None
See application file for complete search history.

(56) References Cited

U.S. PATENT DOCUMENTS 8,088,732 B2    1/2012   Marshall et al.

FOREIGN PATENT DOCUMENTS

| WO | WO 2008088738 A2 * | 7/2008 |
|---|---|---|
| WO | WO 2009025730 A1 * | 2/2009 |

OTHER PUBLICATIONS

Usatine et al. (2010), Am. Fam. Physician, vol. 82(3):249-255.*

* cited by examiner

*Primary Examiner* — Christine J Saoud
*Assistant Examiner* — Jegatheesan Seharaseyon
(74) *Attorney, Agent, or Firm* — Linda O. Palladino; Gail M. Kempler

(57) ABSTRACT

The invention is directed to methods for treating urushiol-induced contact dermatitis. Specifically, the invention is directed to treating and reducing inflammation associated with poison ivy, poison sumac and poison oak by administering to a subject suffering from such conditions novel cellular factor-containing solution compositions (referred to herein as "CFS" compositions), including novel sustained-release cellular factor-containing solution compositions (referred to herein as "SR-CFS" compositions).

4 Claims, No Drawings

METHODS FOR TREATING URUSHIOL-INDUCED CONTACT DERMATITIS

FIELD OF THE INVENTION

The field of the invention is directed to methods for treating urushiol-induced contact dermatitis. Specifically, the field of the invention is directed to treating and reducing inflammation associated urushiol-induced contact dermatitis such as that seen in poison ivy, poison sumac and poison oak, by administering to a subject suffering from such conditions novel cellular factor-containing solution compositions (referred to herein as "CFS" compositions), including novel sustained-release cellular factor-containing solution compositions (referred to herein as "SR-CFS" compositions).

BACKGROUND OF THE INVENTION

Urushiol-induced contact dermatitis (also called *Toxicodendron* dermatitis and Rhus dermatitis) is produced by the oil urushiol. Urushiol is contained in various plants, including the plants of the genus *Toxicodendron*, which includes poison ivy, poison oak, and poison sumac, and certain plants in the family Anacardiaceae, such as mango, Rengas tree, Burmese lacquer tree, India marking nut tree, and the shell of the cashew nut. A few unrelated plants, such as Ginkgo biloba, also contain urushiol.

Symptoms of urushiol-induced contact dermatitis include itching, inflammation, oozing, and in severe cases, a burning sensation. The American Academy of Dermatology estimates there are up to 50 million cases of urushiol-induced dermatitis annually in the United States alone, accounting for 10% of all lost-time injuries in the United States Forest Service.

Urushiol-induced contact dermatitis is contracted by contact with a plant or any other object containing urushiol oil. The oil adheres to almost anything with which it comes in contact, such as skin, towels, blankets and clothing. Materials that contact the plant and then contact the skin are common causes of exposure. Normally, it takes about 24 hours for the rash to first appear. For people who have severe reactions, the rash will worsen during the next few days. Histological examination of urushiol-affected skin shows strong evidence of inflammatory cell migration, e.g. activated lymphocytes, mononuclear cells and fibrosis. In severe reactions, a prednisone prescription is necessary to stop skin damage, especially if the eyes are involved. The rash persists typically for one to two weeks but in some cases can last as long as five weeks. At least 25% of people exposed to urushiol will have very strong responses resulting in severe symptoms. Since the skin reaction is an allergic one, some people may mount progressively stronger reactions after repeated exposures.

Primary treatment involves washing exposed skin thoroughly with soap and water as soon as possible after exposure. Because urushiol is an oil, soap or detergent is necessary to remove it. Antihistamines and hydrocortisone creams or, in severe cases, oral antihistamines, can be used to alleviate the symptoms of the rash. Nonprescription diphenhydramine (Benadryl®) is the most commonly used oral antihistamine. Topical formulations containing diphenhydramine are available, but may cause further irritation to the affected skin. In cases of extreme symptoms, steroids such as prednisone or triamcinolone are sometimes administered. Prednisone is the most commonly prescribed systemic treatment, but can cause serious adrenal suppression changes, so it must be taken carefully. If secondary bacterial infection occurs in the affected area, antibiotics may also be necessary.

It is believed that a treatment option that could reduce inflammation and accelerate the healing of urushiol-induced contact dermatitis, such as that exhibited by poison ivy, poison sumac and poison oak, and not have the associated risks of steroids, especially oral steroids, is desirable. Accordingly, it is an object of the instant invention to provide such a treatment option.

BRIEF SUMMARY OF THE INVENTION

The instant invention provides novel cellular factor-containing solution (CFS) compositions, including Amnion-derived Cellular Cytokine Solution (ACCS), for use in the described methods for treating urushiol-induced contact dermatitis. The instant invention also provides novel sustained-release cellular factor-containing solution (SR-CFS) compositions, including SR-ACCS, for use in the methods. Because the cellular factors are present in the compositions at levels comparable to physiological levels found in the body, they are optimal for use in therapeutic applications which require intervention to support, initiate, replace, accelerate or otherwise influence biochemical and biological processes involved in the treatment and/or healing of disease and/or injury. In the case of the SR-CFS compositions, the cellular factors are released slowly over time to provide a continual, consistent physiologic level of such factors to optimize healing and/or recovery. Detailed information about the compositions used in the methods can be found in U.S. Pat. Nos. 8,058,066 and 8,088,732, both of which are incorporated herein by reference.

Applicants have discovered that Amnion-derived Cellular Cytokine Solution (ACCS) (for details see U.S. Pat. Nos. 8,058,066 and 8,088,732, both of which are incorporated herein by reference) exhibits many anti-inflammatory properties as well as healing properties. Therefore, ACCS, delivered topically as a liquid or ointment, would be expected to be an effective means of treating urushiol-induced contact dermatitis.

Accordingly, a first aspect of the invention is a method for treating urushiol-induced contact dermatitis in a patient in need thereof comprising administering to the patient a therapeutically effective amount of a CFS composition.

A second aspect of the invention is a method for reducing inflammation associated with urushiol-induced contact dermatitis in a patient in need thereof comprising administering to the patient a therapeutically effective amount of a CFS composition such that inflammation associated with urushiol-induced contact dermatitis is reduced.

A third aspect of the invention is a kit comprising a CFS composition and instructions for its use to treat urushiol-induced contact dermatitis.

In a specific embodiment of aspects one-three of the invention, the CFS composition is ACCS.

In another specific embodiment of aspects one-three of the invention the CFS composition, including ACCS, is formulated for topical administration.

In another specific embodiment of aspects one-three of the invention the urushiol-induced contact dermatitis is selected from the group consisting of poison ivy, poison sumac and poison oak.

DEFINITIONS

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristics of secreting a unique combination of physiologically relevant cytokines in a physiologically relevant temporal manner into the extracellular space or into surrounding culture media and which have not been cultured in the presence of any animal-derived products, making them and cell products derived from them suitable for human clinical use. In a preferred embodiment, the ECS cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They have not been cultured in the presence of any non-human animal-derived products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion epithelial cells, from which AMP cells are selected, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods described herein provide improved, novel compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "serum-free" when referring to certain compositions, growth conditions, culture media, etc. described herein, is meant that no animal-derived serum (i.e. no non-human) is used in the preparation, growth, culturing, expansion, storage or formulation of the certain composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium.

As used herein, the term "cellular factor-containing solution" or "CFS" composition means a composition having physiologic concentrations of one or more protein factors. CFS compositions include conditioned media derived from ECS cells, amnion-derived cellular cytokine solution compositions (see definition below), physiologic cytokine solution compositions (see definition below), and sustained release formulations of such CFS compositions.

As used herein, the term "amnion-derived cellular cytokine solution" or "ACCS" means conditioned medium that has been derived from AMP cells or expanded AMP cells.

As used herein, the term "physiologic cytokine solution" or "PCS" composition means a composition which is not cell-derived and which has physiologic concentrations of VEGF, Angiogenin, PDGF and TGF$\beta$2, TIMP-1 and TIMP-2.

As used herein, the term "suspension" means a liquid containing dispersed components, i.e. cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

The term "physiologic" or "physiological level" as used herein means the level that a substance in a living system is found and that is relevant to the proper functioning of a biochemical and/or biological process.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "therapeutically effective amount" means that amount of a therapeutic agent necessary to achieve a desired physiological effect (i.e. treating urushiol-induced contact dermatitis).

As used herein, the term "pharmaceutically acceptable" means that the components, in addition to the therapeutic agent, comprising the formulation, are suitable for administration to the patient being treated in accordance with the present invention.

As used herein, the term "therapeutic component" means a component of the composition which exerts a therapeutic benefit when the composition is administered to a subject.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time release capsules and the like.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

As used herein, the term "enteral" administration means any route of drug administration that involves absorption of the drug through the gastrointestinal tract. Enteral administration may be divided into three different categories, oral, gastric, and rectal. Gastric introduction involves the use of a tube through the nasal passage or a tube in the abdomen leading directly to the stomach.

As used herein, the term "topical" administration means a medication that is applied to body surfaces such as the skin or mucous membranes to treat ailments via a large range of classes including but not limited to liquids, sprays, creams, foams, gels, lotions, salves and ointments.

The terms "sustained-release", "extended-release", "time-release", "controlled-release", or "continuous-release" as used herein means an agent, typically a therapeutic agent or drug, that is formulated to dissolve slowly and be released over time.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model" refers to any art-accepted animal model in which the compositions of the invention exhibit efficacy.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Compositions and Methods of Making Compositions

Detailed information and methods on the preparation of AMP cell compositions, generation of ACCS, generation of pooled ACCS, detection of cytokines in non-pooled and pooled ACCS using ELISA, generation of PCS compositions, and generation of sustained-release CFS compositions can be found in U.S. Pat. Nos. 8,058,066 and 8,088,732, both of which are incorporated herein by reference.

The invention provides for an article of manufacture comprising packaging material and a pharmaceutical composition of the invention contained within the packaging material, wherein the pharmaceutical composition comprises CFS compositions, including ACCS. The packaging material comprises a label or package insert which indicates that the CFS compositions, including ACCS, contained therein can be used for therapeutic applications such as, for example, treating urushiol-induced contact dermatitis.

Formulation, Dosage and Administration of CFS Compositions

Compositions comprising CFS compositions may be administered to a subject to provide various cellular or tissue functions, for example, to prevent or treat nasal polyps. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. For topical administration, the CFS compositions may be formulated as a spray, liquid, cream, foam, gel, lotion, salve, and ointment, etc. The compositions may also be administered to the recipient in one or more physiologically acceptable carriers. Carriers for CFS compositions may include but are not limited to solutions of normal saline, phosphate buffered saline (PBS), lactated Ringer's solution containing a mixture of salts in physiologic concentrations, or cell culture medium.

In addition, one of skill in the art may readily determine the appropriate dose of the CFS compositions for a particular purpose. A preferred dose is in the range of about 0.1-to-1000 micrograms per square centimeter of applied area. Other preferred dose ranges are 1.0-to-50.0 micrograms/applied area. In a particularly preferred embodiment, it has been found that relatively small amounts of the CFS compositions are therapeutically useful. One exemplification of such therapeutic utility is the ability for ACCS (including pooled ACCS) to accelerate wound healing (for details see U.S. Publication No. 2006/0222634 and U.S. Pat. No. 8,187,881, both of which are incorporated herein by reference). One of skill in the art will also recognize that the number of doses to be administered needs also to be empirically determined based on, for example, severity and type of disease, disorder or injury being treated; patient age, weight, sex, health; other medications and treatments being administered to the patient; and the like. For example, in a specific embodiment, one dose is sufficient to have a therapeutic effect (i.e. treating urushiol-induced contact dermatitis). Other specific embodiments contemplate, 2, 3, 4, or more doses for therapeutic effect.

One of skill in the art will also recognize that number of doses (dosing regimen) to be administered needs also to be empirically determined based on, for example, severity and type of injury, disorder or condition being treated; patient age, weight, sex, health; other medications and treatments being administered to the patient; and the like. In addition, one of skill in the art recognizes that the frequency of dosing needs to be empirically determined based on similar criteria. In certain embodiments, one dose is administered every day for a given number of days (i.e. once a day for 7 days, etc.). In other embodiments, multiple doses may be administered in one day (every 4 hours, etc.). Multiple doses per day for multiple days are also contemplated by the invention.

In further embodiments of the present invention, at least one additional agent may be combined with the CFS compositions. Such agents may act synergistically with the CFS compositions of the invention to enhance the therapeutic effect. Such agents include but are not limited to growth factors, cytokines, chemokines, antibodies, inhibitors, antibiotics, immunosuppressive agents, steroids, anti-fungals, anti-virals or other cell types (i.e. stem cells or stem-like cells, for example, AMP cells). Inactive agents include carriers, diluents, stabilizers, gelling agents, delivery vehicles, ECMs (natural and synthetic), scaffolds, and the like. When the CFS compositions are administered conjointly with other pharmaceutically active agents, even less of the CFS compositions may be needed to be therapeutically effective.

CFS compositions may also be inserted into a delivery device, e.g., a tube, in different forms. For example, the CFS compositions can be part of a solution contained in such a delivery device. As used herein, the term "solution" includes a pharmaceutically acceptable carrier or diluent. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and may optionally be preserved against the contaminating action of microorganisms such as bacteria and fungi through the use of, for example, parabens, chlorobutanol, phenol, ascorbic acid, thimerosal, and the like. Solutions of the invention can be prepared by incorporating the CFS compositions in a pharmaceutically acceptable carrier or diluent and, as required, other ingredients enumerated above.

The timing of administration of CFS compositions will depend upon the type and severity of the disease, disorder, or injury being treated. In one embodiment, the CFS compositions are administered as soon as possible after onset of symptoms or diagnosis. In another embodiment, CFS compositions are administered more than one time following onset of symptoms or diagnosis.

Support matrices, scaffolds, membranes and the like into which the CFS compositions can be incorporated or embedded include matrices which are recipient-compatible and which degrade into products which are not harmful to the recipient. Detailed information on suitable support matrices, etc. can be found in U.S. Pat. Nos. 8,058,066 and 8,088,732, both of which are incorporated herein by reference.

A "therapeutically effective amount" of a therapeutic agent within the meaning of the present invention will be determined by a patient's attending physician or veterinarian. Such amounts are readily ascertained by one of ordinary skill in the art and will enable preventing or treating hemorrhoids when administered in accordance with the present invention. Factors which influence what a therapeutically effective amount will be include, the specific activity of the therapeutic agent being used, the extent of the surgical wound, the absence or presence of infection, time elapsed since the surgery, and the age, physical condition, existence of other disease states, and nutritional status of the patient. Additionally, other medication the patient may be receiving will effect the determination of the therapeutically effective amount of the therapeutic agent to administer.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

The following examples provide evidence of the anti-inflammatory and wound healing effects of ACCS is several different inflammatory conditions (mucosal, mucosal/infected; skin (intact and lesioned); and cutaneous wound/infected), thus providing strong evidence for the broad applicability of ACCS to prevent and/or treat inflammatory conditions.

Example 1

Inflammatory Model—Use of ACCS to Prevent Onset of Periodontal Disease in an Animal Model Objective: The aim of this study was to evaluate the preventive role of ACCS in *Porphyromonas gingivalis* (*P. gingivalis*)-induced experimental periodontitis in rabbits Methods: Eight New-Zealand White rabbits were distributed into 3 groups: 1. Untreated (n=2), 2. Control (unconditioned ACCS culture media) (n=3), and 3. ACCS (n=3). At baseline, all rabbits received silk ligatures bilaterally tied around mandibular second premolars under general anesthesia. The assigned test materials, ACCS or control, in volumes of 10 μL were topically applied to the ligated sites with a blunt needled-Hamilton Syringe from the time of ligature; control animals received ligature, but no treatment. Topical *P. gingivalis*-containing slurry (1 mL) was subsequently applied to induce the periodontal inflammation. The application of test materials and *P. gingivalis* continued for 6 weeks on an every-other-day schedule. At 6 weeks, following euthanasia, the mandibles were surgically harvested. Morphometric, radiographic and histologic evaluations were performed.

Results: Macroscopic evaluations including soft tissue assessments, crestal bone and infrabony measurements showed significant periodontal breakdown induced by *P. gingivalis* in control and no treatment groups at 6 weeks compared to historical ligature-alone groups (p=0.05, p=0.03, respectively). ACCS application significantly inhibited soft tissue inflammation and prevented both crestal bone loss and infrabony defect formation compared to untreated and control groups (p=0.01, p=0.05, respectively). Histologic assessments and histomorphometric measurements supported the clinical findings; ACCS treated animals demonstrated significantly less inflammation in soft tissue and less bone loss compared to the untreated and control groups (p=0.05).

Conclusions: Topical ACCS application prevents periodontal inflammatory changes and bone loss induced by *P. gingivalis* as shown both at clinical and histopathological level. ACCS has potential as a therapeutic approach for the prevention of periodontal diseases Example 2

Inflammatory Model—Use of ACCS to Stop Progression of or Reverse Periodontal Disease in an Animal Model Objective: The aim of this study was to evaluate the therapeutic actions of ACCS in the treatment of periodontitis induced by *P. gingivalis*.

Methods: The study was conducted using a two-phase rabbit periodontitis protocol: 1-Disease induction (6 weeks) and 2—Treatment (6 weeks). Periodontal disease was induced in 16 New-Zealand White rabbits by every-other-day application of topical *P. gingivalis* to ligatured mandibular premolars. At the end of Phase 1, 4 randomly selected rabbits were sacrificed to serve as the baseline disease group. For Phase 2, the remaining 12 rabbits were distributed into 3 groups (n=4), 1—Untreated, 2—Control (unconditioned ACCS culture media) and 3—ACCS treatment. At the end of Phase 2, morphometric, radiographic and histologic evaluations were performed on harvested mandibles.

Results: The baseline disease group exhibited experimental periodontitis evidenced by tissue inflammation and bone loss. At the end of Phase 2, the untreated group showed significant disease progression characterized by increased soft and hard tissue destruction (p=0.05). The tissue inflammation and bone loss was significantly reduced by topical ACCS compared to baseline disease and untreated groups (p=0.05; p=0.002, respectively). The control treatment also arrested disease progression compared to untreated group (p=0.01), but there was no improvement in periodontal health compared to baseline disease (p=0.4). Histopathological assessments revealed similar findings; ACCS stopped the progression of inflammatory process (p=0.003) and reversed bone destruction induced by *P. gingivalis* (p=0.008). The ACCS-treated group had minimal osteoclastic activity limited to crestal area compared to untreated and control groups, which showed a profound osteoclastogenic activity at the bone crest as well as at interproximal sites.

Conclusions: Topical application of ACCS stopped the progression of periodontal inflammation and resulted in tissue regeneration in rabbit periodontitis indicating its potential therapeutic efficacy.

Example 3

Inflammatory Model—Evaluate the Efficacy of Topically Applied ACCS to Inhibit Irritant 12-O-tetradecanoylphorbol-13-Acetate (TPA) Skin Inflammation in Mice Method: Topical treatment was given twice daily to the following groups: 1. TPA+topical control; 2. TPA+ACCS; 3. TPA+clobetasol 0.05 topical solution (the strongest available topical corticosteroid); 4. ACCS alone; 5. No treatment (the other untreated ear was measured). The endpoints for the study were ear thickness and ear weight at the end of the experiment. The thicker the ear and the more it weighs correlates with the degree of inflammation.

Results: Topically applied ACCS was effective at reducing the inflammation induced by TPA. The anti-inflammatory activity of topical ACCS reached the same level as clobetasol (a class 1 potent topical corticosteroid) by 3 days after beginning application.

Conclusion: ACCS has a strong anti-inflammatory effect when applied to skin.

Example 4

Inflammatory Model—Evaluate the Efficacy of Intralesional Injection of ACCS to Inhibit Irritant (TPA) Skin Inflammation in Mice Method: Intralesional injection into the ear was given once daily to the following groups: 1. TPA+intralesional control; 2. TPA+intralesional ACCS; 3. TPA+intralesional kenalog (10 mg/ml) (a potent intralesional corticosteroid); 4. ACCS intralesional injection alone; 5. Saline sham injections to the normal untreated ear. The endpoints for the study were ear thickness and ear weight at the end of the experiment. The thicker the ear and the more it weighs correlates with the degree of inflammation.

Results: Intralesional injection of ACCS was effective at reducing the inflammation induced by TPA at all time points beginning on day 2 of daily injections. Intralesional kenalog (10 mg/ml) injections induced a hematoma at the site of injection, which led to some inflammation and that is why there is not a substantial difference in ear thickness when comparing TPA+kenalog with TPA+control.

Conclusions: Intralesional ACCS did reduce skin inflammation but the topically applied ACCS in Example 1 above had a more potent effect. There was no difference in ear weight using either ACCS or intralesional kenalog compared with TPA+control.

Example 5

Wound Healing Model—Effects of ACCS in an Animal Model of Chronic Wound Healing

An art-accepted animal model for chronic granulating wound was used to study the effects of ACCS on chronic wound healing (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990.).

Results: ACCS was effective in not allowing proliferation of tissue bacterial bioburden. ACCS allowed accelerated healing of the granulating wound significantly faster than the non-treated infected control groups (Franz, M., et al., ePlasty Vol. 8, pp. 188-199, Apr. 11, 2008).

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification

What is claimed is:

1. A method for reducing inflammation associated with urushiol-induced contact dermatitis in a patient in need thereof comprising topically administering to the patient about 0.1-to-1000 micrograms per square centimeter of applied area a compositions selected from the group consisting of an Extraembryonic Cytokine-containing Solution (ECS) composition, Amnion derived Cellular Cytokine Solution (ACCS), Physiologic Cytokine Solution (PCS), and sustained release (SR) formulations of ECS, ACCS and PCS, such that inflammation associated with urushiol-induced contact dermatitis is reduced, wherein the ECS, ACCS, PCS, and SR-formulations of ECS, ACCS and PCS comprise about 5-16 ng/mL VEGF, about 3.5-4.5 ng/mL Angiogenin, about 100-165 pg/mL PDGF, about 2.5-2.7 ng/mL TGFβ2, about 0.68 µg/mL TIMP-1 and about 1.04 µg/mL TIMP-2.

2. The method of claim 1 wherein the administered composition is ACCS.

3. The method of claim 1 wherein the are ECS, ACCS, PCS, and SR-formulations of ECS, ACCS and PCS are formulated for topical administration.

4. The method of claim 1 wherein the urushiol-induced contact dermatitis is selected from the group consisting of poison ivy, poison sumac and poison oak.

* * * * *